(12) United States Patent
Dominguez

(10) Patent No.: US 9,700,719 B1
(45) Date of Patent: Jul. 11, 2017

(54) DEVICE USING ELECTROTHERAPY FOR THE RELIEF OF HEMORRHOID INFLAMMATION

(71) Applicant: Yamil Dominguez, Tampa, FL (US)

(72) Inventor: Yamil Dominguez, Tampa, FL (US)

( * ) Notice: Subject to any disclaimer, the term of this patent is extended or adjusted under 35 U.S.C. 154(b) by 0 days.

(21) Appl. No.: 15/188,700

(22) Filed: Jun. 21, 2016

(51) Int. Cl.
*A61N 1/05* (2006.01)
*A61N 1/36* (2006.01)
*A61N 1/372* (2006.01)
*A61N 1/378* (2006.01)

(52) U.S. Cl.
CPC ....... *A61N 1/36007* (2013.01); *A61N 1/0512* (2013.01); *A61N 1/3787* (2013.01); *A61N 1/37217* (2013.01); *A61N 1/37247* (2013.01)

(58) Field of Classification Search
CPC .......................... A61N 1/36007; A61N 1/0512
See application file for complete search history.

(56) References Cited

U.S. PATENT DOCUMENTS

| | | | | |
|---|---|---|---|---|
| 4,542,753 A | * | 9/1985 | Brenman | A61F 5/41 29/825 |
| 4,898,169 A | * | 2/1990 | Norman | A61B 1/31 606/42 |
| 2003/0055465 A1 | * | 3/2003 | Ben-Haim | A61N 1/32 607/40 |
| 2008/0208188 A1 | * | 8/2008 | Cao | A61N 1/205 606/41 |
| 2014/0303692 A1 | * | 10/2014 | Pignatelli | A61N 5/0613 607/89 |
| 2015/0134026 A1 | * | 5/2015 | Kaula | A61N 1/0551 607/41 |

\* cited by examiner

*Primary Examiner* — Eric D. Bertram
(74) *Attorney, Agent, or Firm* — Jesus Sanchelima; Christian Sanchelima

(57) ABSTRACT

A device to relieve hemorrhoid inflammation using electrotherapy including a capsule insertable into a user's anus a predetermined depth, a control unit having a power indicator and power button, the control unit including modulating means for a user to control the intensity and duration of the therapy session. The device also includes a wire that connects the control unit to the capsule. In an alternate embodiment, the device can implement Bluetooth technology to send instructions from the control unit to the capsule wirelessly to actuate it so that it can deliver electrotherapy to a user's anus. A mobile application on a mobile device can be used to control the electrotherapy being sent to a user through the capsule.

10 Claims, 4 Drawing Sheets

60

40

DEVICE USING ELECTROTHERAPY FOR THE RELIEF OF HEMORRHOID INFLAMMATION

BACKGROUND OF THE INVENTION

1. Field of the Invention

The present invention relates to a device to treat hemorrhoid inflammation and, more particularly, to such a device that uses electrotherapy to relieve hemorrhoid inflammation.

2. Description of the Related Art

Several designs for a hemorrhoid relief device have been designed in the past. None of them, however, include a device that can be connected wirelessly or wired to a control unit to provide electrotherapy stimulation to a user's anus, thereby relieving inflammation and accompanying discomfort.

Applicant believes that a related reference corresponds to U.S. patent application No. US20120029602 filed by Vascular Technologies, Inc. for a method, apparatus, and system for treatment of hemorrhoidal disease using negative galvanism. However, it differs from the present invention because the Vascular reference teaches of a device that must be held against the anus by a user. The user does not have his hands free but instead must intrusively maintain the device in the desired position notwithstanding the fatigue associated with doing so. The present invention addresses this unsolved problem by creating a capsule that is inserted into a user's anus a predetermined depth. The capsule is connected to a control unit where a user can modulate the amount of stimulation without affecting the placement of the device. With the prior art the device would have to be removed from the inflammation site to be modulated.

Other documents describing the closest subject matter provide for a number of more or less complicated features that fail to solve the problem in an efficient and economical way. None of these patents suggest the novel features of the present invention.

SUMMARY OF THE INVENTION

It is one of the main objects of the present invention to provide a device that relieves hemorrhoid inflammation using electrotherapy.

It is another object of this invention to provide such a device that is inserted into a user's anus allowing hands free operation.

It is still another object of the present invention to provide such a device having a control unit that is connected wired or wirelessly to a capsule inserted into a user's anus that can be modulated to a desired intensity determined by the user.

It is yet another object of this invention to provide such a device that is inexpensive to implement and maintain while retaining its effectiveness.

Further objects of the invention will be brought out in the following part of the specification, wherein detailed description is for the purpose of fully disclosing the invention without placing limitations thereon.

BRIEF DESCRIPTION OF THE DRAWINGS

With the above and other related objects in view, the invention consists in the details of construction and combination of parts as will be more fully understood from the following description, when read in conjunction with the accompanying drawings in which.

DETAILED DESCRIPTION OF THE EMBODIMENTS OF THE INVENTION

Figure 1:
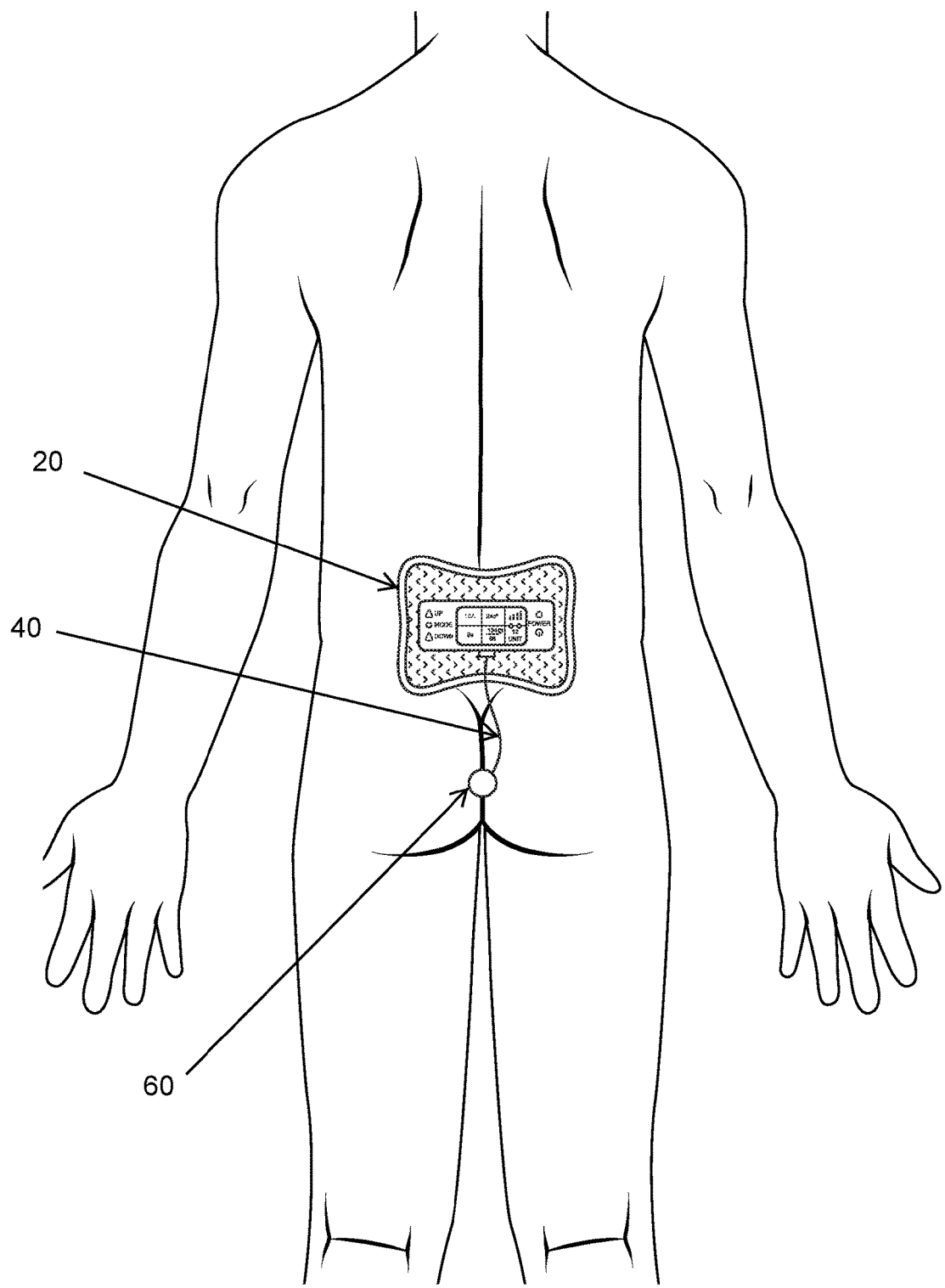
FIG. 1 represents a front elevational view of the device having the control unit mounted to the lower back of the user and connected to a capsule inserted into a user's anus through a wire.
Figure 2:
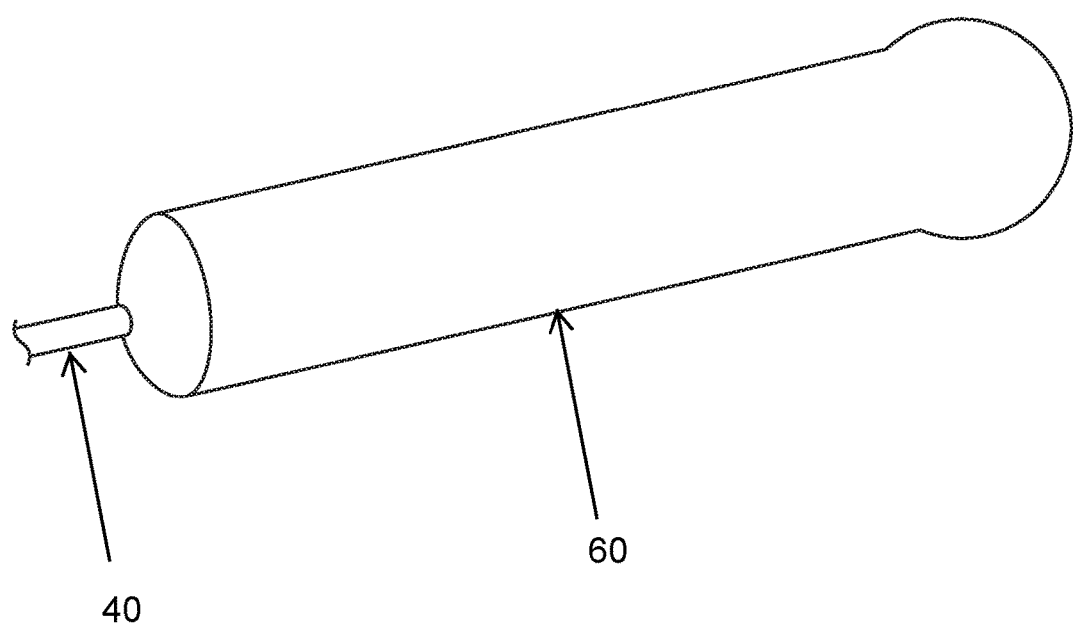
FIG. 2 shows an isometric view of the capsule without the wire or control unit shown.
Figure 3:
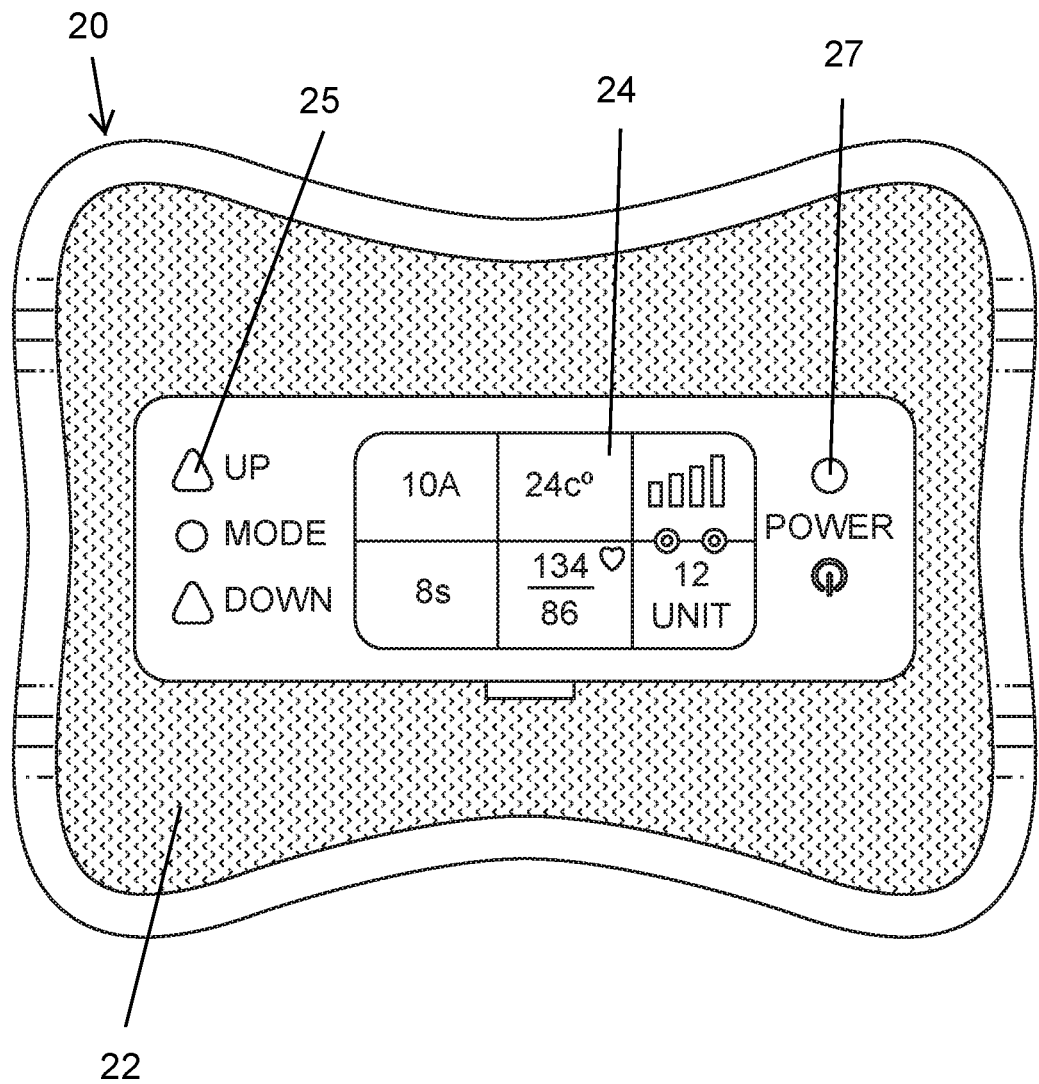
FIG. 3 illustrates a front elevational view of the control unit showing the power switch, power indicator, touchscreen display, and buttons used to modulate the intensity and/or the duration and rhythm of electrotherapy.
Figure 4:
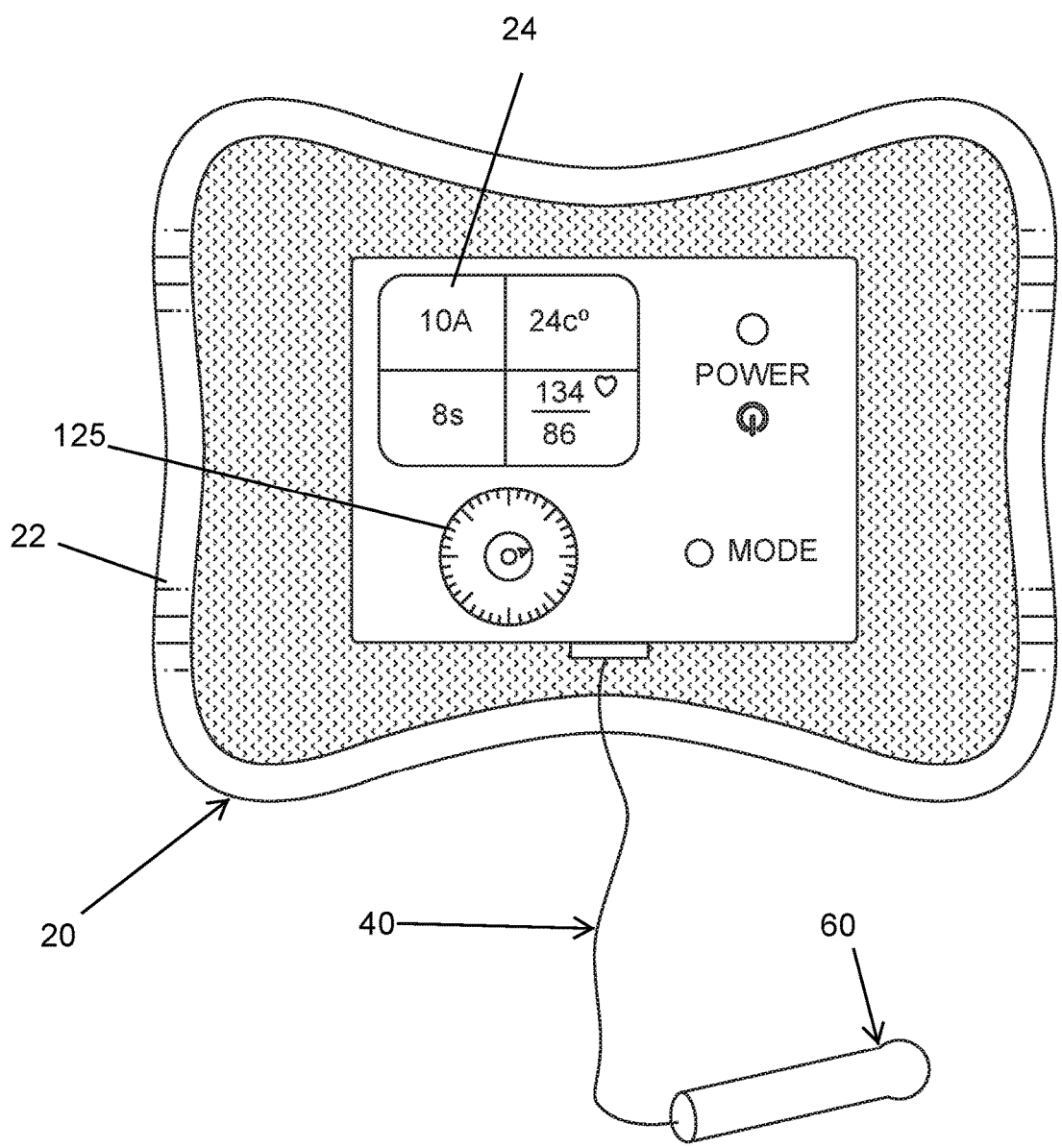
FIG. 4 is a representation of an alternate embodiment of the present invention wherein the control module includes a modulating dial instead of a touchscreen to adjust the intensity of the electrotherapy.

Referring now to the drawings, where the present invention is generally referred to with numeral 10, it can be observed that it basically includes control unit assembly 20, connection means 40, and capsule assembly 60. As shown in FIGS. 1, 3 and 4, control unit assembly 20 includes control unit member 22 being mounted to a predetermined location on a user's body such as the lower back. Control unit member 22 can be mounted to the user's body using a strap, adhesive gel, acrylate, including methacrylates and epoxy diacrylates (which are also known as vinyl resins), or similar means. Control unit member 22 further includes a plurality of sensors and reading displays 24. Intensity control buttons 25 are used to increase or decrease the intensity of the electrotherapy being transmitted to capsule assembly 60. Power button 27 is also used to activate the device.

Mode control button 26 is used to alternate the rhythm and pattern that the electrotherapy is transmitted to capsule 60. Reading displays 24 can provide various information such as heart rate, blood pressure, intensity level, body temperature, duration of the therapy, etc. These readings can be done with corresponding sensors located on the inside of control unit member 22.

As shown in FIG. 4, control unit assembly 20 is connected to capsule assembly 60 using connection means 40. Capsule assembly 60 has a shape that is configured to cooperate with the anus of a user so that it can be inserted comfortably and snuggly. Capsule assembly 60 is of a predetermined length and width to interact with the areas that require relief due to hemorrhoidal inflammation. Electrical energy is transmitted to capsule 60 using connection means 40 to provide electrotherapy to a user.

Control unit member 22 includes an internal rechargeable battery that acts as the source of the electrical energy. In one embodiment, the battery can be recharged using a USB port on control unit member 22. The battery can also be charged using a charging dock. In one embodiment, shown in FIG. 4, intensity buttons 25 can be in analog form using a dial 125. Connection means 40 is of a length that cooperates with the distance between control unit member 22 and capsule assembly 60.

In one embodiment, a user can control intensity buttons 25 and power button 27 using a mobile application on their mobile device. Using the mobile application a user can turn on and off the device or increase or decrease the intensity of electrical energy. Also, the readings on display readings 24 can be displayed on the mobile application. In another embodiment, connection means 40 is wireless and capsule 60 can be fitted with its own battery so that electrotherapy is originated in capsule 60 and delivered straight to the user therefrom. In this embodiment, capsule 60 can include a Bluetooth receiver that receives instructions from a Bluetooth transmitter on a remote control or through a mobile application operated by a user.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

What is claimed is:

1. A device to relieve hemorrhoids comprising: a capsule that is adapted to be inserted into a user's anus, a patch-like control unit member with electrotherapy intensity modulation, said capsule includes electrodes to provide electrotherapy configured to relieve hemorrhoids, said capsule having a shape that allows it to remain in place on its own within the anus said capsule wirelessly connected to said control unit member, said control unit member having a battery, reading displays, intensity buttons, and a power button, said control unit member configured to be attached to a user's back using an adhesive, said control unit controlling an intensity of the electrotherapy provided by the capsule inside said user's anus, a downloadable software program on a mobile device used to modulate said electrotherapy, provide said reading displays, and power on and off the electrotherapy delivered by said capsule, wherein the mobile device is a separate component from the control unit member.

2. The device subject of claim 1 wherein a remote control is used to modulate the electrotherapy delivered by said capsule, said remote also powers on and off the electrotherapy.

3. The device subject of claim 1 wherein said mounting means is a strap.

4. The device subject of claim 1 wherein said intensity buttons increase and decrease the intensity of electrotherapy delivered to a user.

5. The device subject of claim 1 wherein said battery is rechargeable.

6. The device subject of claim 1 wherein said intensity buttons are digital.

7. The device subject of claim 1 wherein said intensity buttons are analog.

8. The device subject of claim 1 wherein said control unit member includes sensors that read a user's blood pressure, heart rate, therapy duration, or body temperature.

9. The device subject of claim 1 wherein said control unit member is controlled using a mobile application on a mobile device.

10. The device of claim 1 wherein said connection means is a wired connection.

* * * * *